(12) United States Patent
Yoshida et al.

(10) Patent No.: US 7,964,540 B2
(45) Date of Patent: Jun. 21, 2011

(54) LUBE BASE OIL AND LUBRICATING OIL COMPOSITION

(75) Inventors: Yukio Yoshida, Sodegaura (JP);
Toshiyuki Tsubouchi, Sodegaura (JP);
Hiroki Sekiguchi, Sodegaura (JP);
Hidetoshi Koga, Ichihara (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 1479 days.

(21) Appl. No.: 10/574,491

(22) PCT Filed: Oct. 6, 2004

(86) PCT No.: PCT/JP2004/014735
§ 371 (c)(1),
(2), (4) Date: Apr. 3, 2006

(87) PCT Pub. No.: WO2005/035699
PCT Pub. Date: Apr. 21, 2005

(65) Prior Publication Data
US 2007/0042915 A1 Feb. 22, 2007

(30) Foreign Application Priority Data
Oct. 8, 2003 (JP) ................................. 2003-349816

(51) Int. Cl.
*C10M 169/04* (2006.01)
*C07C 13/00* (2006.01)
*C07C 13/615* (2006.01)

(52) U.S. Cl. .............. 508/110; 585/20; 585/21; 585/22; 585/23

(58) Field of Classification Search .................. 508/110, 508/343; 585/20, 21, 22, 23
See application file for complete search history.

(56) References Cited

U.S. PATENT DOCUMENTS

| | | | |
|---|---|---|---|
| 2,382,038 A | 8/1945 | Bruson | |
| 2,940,984 A | 6/1960 | Applequist et al. | |
| 3,411,369 A | 11/1968 | Hammann et al. | |
| 3,803,037 A * | 4/1974 | Wygant | 508/371 |
| 6,320,088 B1 * | 11/2001 | Matsuno et al. | 585/21 |
| 7,132,582 B2 * | 11/2006 | Jasra et al. | 585/668 |
| 7,402,715 B2 * | 7/2008 | Yoshida et al. | 585/1 |

FOREIGN PATENT DOCUMENTS

EP 0 082 967 A2 7/1983
(Continued)

OTHER PUBLICATIONS

Machine Translation of EP82967 A2, Vojacek et al, Jul. 1983.*
N. V. Elagina, et al., "The catalytic transformation of 1,4-endomethylenespiro [5,5] undecane on a platinum catalyst", Chemical Abstracts Service, Apr. 22, 2001, 1 page, XP002491332, & Neftekhimiya (1965), 5 (5), 671-5 CODEN: NEFTAH; ISSN: 0028-2421, 1965.

Joseph Casanova, et al., "Transannular carbene insertion reactions in the bicyclo [4.2.1] nonane system", J. Org. Chem.,vol. 44, No. 22, Sep. 1977, pp. 3976-3979, XP002491325.

(Continued)

*Primary Examiner* — Glenn A Caldarola
*Assistant Examiner* — Vishal Vasisth
(74) *Attorney, Agent, or Firm* — Oblon, Spivak, McClelland, Maier & Neustadt, L.L.P.

(57) ABSTRACT

A lube base oil which comprises at least one hydrocarbon compound having as the basic skeleton a structure represented by any of the general formulae (I) to (VI) and has a viscosity at −40° C. of 40 Pa·s or lower and a viscosity index of 80 or higher, (wherein p is an integer of 1 to 10, provided that in the formulae (I) and (II), p is not 1). It satisfies the coefficient of high-temperature traction, low-temperature flowability, and viscosity index on a high level.

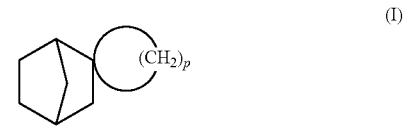

(I)

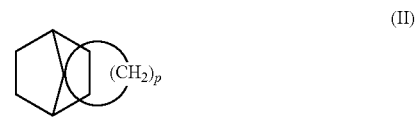

(II)

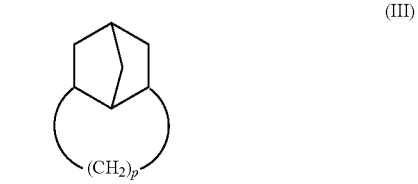

(III)

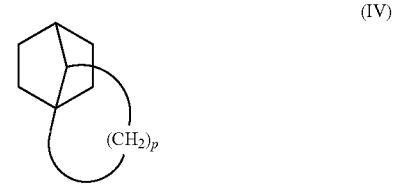

(IV)

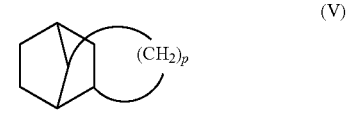

(V)

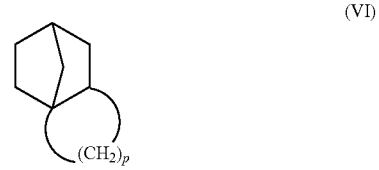

(VI)

18 Claims, No Drawings

FOREIGN PATENT DOCUMENTS

| | | |
|---|---|---|
| EP | 0 989 177 A1 | 3/2000 |
| FR | 2 036 999 | 12/1970 |
| JP | 58-154799 | 9/1983 |
| JP | 09-059660 | 3/1997 |
| JP | 2000-017280 | 1/2000 |
| JP | 2001-247492 | 9/2001 |
| JP | WO03014268 * | 2/2003 |

OTHER PUBLICATIONS

M. Ohscgi, et al., "One-step bridgehead acetamidation of polycycloalkanes through bromine oxidation", Synthesis, Communications, 1997, pp. 632-633, XP002491326.

Y. Tobe, et al., "Adamantane rearrangement of [3.3.2] propellanes" J. Am. Chem. Soc., vol. 103, No. 9, 1981, pp. 2307-2309, XP002491327.

H. Musso, et al., "Hydrogenolyse kleiner Kohlenstoffringe, XIV Die Hydrierung des Deltacyclans", Chemische Berichte, vol. 119, 1986, pp. 2362-2366, XP002491328.

A. M. Klester, et al., "The Adamantane rearrangement of 1, 2-Trimethylenenorbornanes", Helvetica Chimica Acta, vol. 68, 1985, pp. 104-109, XP002491329.

R. Ranganathan, et al., "studies in sesquiterpenes-XL* Isolongifolene (Part 1): Structure", Tetrahedron, vol. 26, 1970, pp. 621-630, XP002491330.

E. Osawa, et al., "The mechanisms of carbonium ion rearrangements of tricycloundecanes elucidated by empirical force field calculations", J. Am. Chem. Soc., XP002491331, vol. 99, No. 16, Aug. 3, 1977, pp. 5361-5373.

* cited by examiner

LUBE BASE OIL AND LUBRICATING OIL COMPOSITION

This application is a 371 of PCT/JP04/14735, filed Oct. 6, 2004.

TECHNICAL FIELD

The present invention relates to a lube base oil and a lubricating oil composition. More particularly, the present invention is directed to a lube base oil and a lubricating oil composition which are useful as a fluid for traction drive and which exhibit well-balanced properties, i.e. a high high-temperature traction coefficient which is important for practical application to CVT (continuously variable transmission) for automobiles, a low low-temperature viscosity which is important for starting engines at low temperatures, and a high viscosity index.

BACKGROUND ART

Since traction type CVT for automobiles has a large torque transmission capacity and is used under severe conditions, it is essential from the standpoint of the power transmission that the traction coefficient of a traction oil used therefor must be sufficiently greater than the minimum value in the temperature range in which the oil is used, namely the traction coefficient at a high temperature (120° C.) must be sufficiently greater than the value prescribed in the design of CVT.

Since the traction oil also assumes a role as an ordinary lubricant oil in CVT, it is necessary that the traction oil has a high viscosity sufficient to maintain an oil film even at a high temperature in order to prevent frictional abrasion. On the other hand, the traction oil must have a low viscosity even at a low temperature (low-temperature fluidity) in order to provide low temperature startability in cold areas such as in northern America and northern Europe. Stated otherwise, the temperature dependency of the viscosity must be small, namely the viscosity index must be high.

In view of the foregoing background, the present inventors developed a base oil compound for a high performance traction oil exhibiting such high high-temperature traction coefficient, high viscosity index and excellent low-temperature fluidity which were not achieved before (see Patent document 1).

However, a design of CVT requires that the high-temperature traction coefficient, low-temperature fluidity and viscosity index must be satisfied at a still higher level.

Patent document 1: Japanese Patent Application Laid-Open No. 17280/2000

DISCLOSURE OF THE INVENTION

The present invention has been made in view of the above circumstance and has as its object the provision of a lube base oil and a lubricating oil composition which satisfy the coefficient of high-temperature traction, low-temperature fluidity and viscosity index at a high level.

As a result of the earnest study by the present inventors, it has been found that the object of the present invention is fulfilled by using a specific hydrocarbon compound having a bicyclo[2.2.1]heptane ring. The present invention has been completed on the basis of this finding.

Thus, the gist of the present invention is as follows.

1. A lube base oil characterized in that the lube base oil comprises at least one hydrocarbon compound having, as a basic skeleton, a structure represented by any of the general formulas (I) to (VI) shown below and has a viscosity at −40° C. of 40 Pa·s or lower and a viscosity index of 80 or higher.

[1]

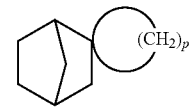
(I)

(II)

(III)

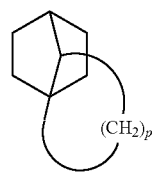
(IV)

(V)

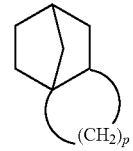
(VI)

wherein p is an integer of 1 to 10 with the proviso that, in the formulas (I) and (II), p is not 1.

2. A lube base oil as recited in 1 above and having a viscosity at −40° C. of 35 Pa·s or lower.

3. A lube base oil as recited in 1 or 2 above, wherein the hydrocarbon compound having, as a basic skeleton, the structure represented by the general formula (I) is a hydrocarbon compound which has 12 to 24 carbon atoms and which is represented by the following general formula (a):

[2]

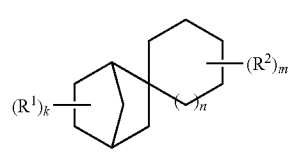
(a)

wherein k, m and n are each an integer of 0 to 6 with the proviso that k+m is an integer of 0 to 6, and $R^1$ and $R^2$ each represent an alkyl group having 1 to 4 carbon atoms or a cycloalkyl group having 5 to 12 carbon atoms, or are taken together to represent an alkylene group having 1 to 7 carbon atoms.

4. A lube base oil as recited in 1 or 2 above, wherein the hydrocarbon compound having, as a basic skeleton, the structure represented by the general formula (II) is a hydrocarbon compound which has 12 to 24 carbon atoms and which is represented by the following general formula (b):

[3]

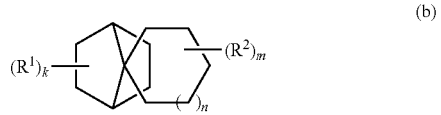
(b)

wherein k, m and n are each an integer of 0 to 6 with the proviso that k+m is an integer of 0 to 6, and $R^1$ and $R^2$ each represent an alkyl group having 1 to 4 carbon atoms or a cycloalkyl group having 5 to 12 carbon atoms, or are taken together to represent an alkylene group having 1 to 7 carbon atoms.

5. A lube base oil as recited in 1 or 2 above, wherein the hydrocarbon compound having, as a basic skeleton, the structure represented by the general formula (III) is a hydrocarbon compound which has 12 to 24 carbon atoms and which is represented by the following general formula (c):

[4]

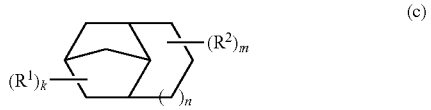
(c)

wherein k, m and n are each an integer of 0 to 6 with the proviso that k+m is an integer of 0 to 6, and $R^1$ and $R^2$ each represent an alkyl group having 1 to 4 carbon atoms or a cycloalkyl group having 5 to 12 carbon atoms, or are taken together to represent an alkylene group having 1 to 7 carbon atoms.

6. A lube base oil as recited in 1 or 2 above, wherein the hydrocarbon compound having, as a basic skeleton, the structure represented by the general formula (IV) is a hydrocarbon compound which has 12 to 24 carbon atoms and which is represented by the following general formula (d):

[5]

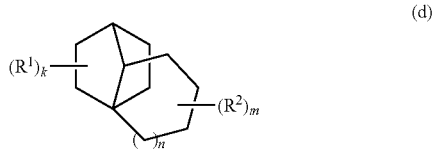
(d)

wherein k, m and n are each an integer of 0 to 6 with the proviso that k+m is an integer of 0 to 6, and $R^1$ and $R^2$ each represent an alkyl group having 1 to 4 carbon atoms or a cycloalkyl group having 5 to 12 carbon atoms, or are taken together to represent an alkylene group having 1 to 7 carbon atoms.

7. A lube base oil as recited in 1 or 2 above, wherein the hydrocarbon compound having, as a basic skeleton, the structure represented by the general formula (V) is a hydrocarbon compound which has 12 to 24 carbon atoms and which is represented by the following general formula (e):

[6]

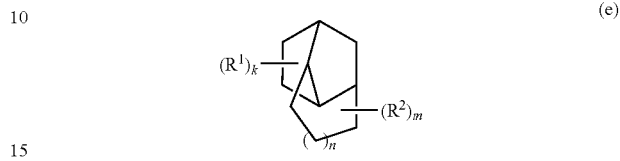
(e)

wherein k, m and n are each an integer of 0 to 6 with the proviso that k+m is an integer of 0 to 6, and $R^1$ and $R^2$ each represent an alkyl group having 1 to 4 carbon atoms or a cycloalkyl group having 5 to 12 carbon atoms, or are taken together to represent an alkylene group having 1 to 7 carbon atoms.

8. A lube base oil as recited in 1 or 2 above, wherein the hydrocarbon compound having, as a basic skeleton, the structure represented by the general formula (VI) is a hydrocarbon compound which has 12 to 24 carbon atoms and which is represented by the following general formula (f):

[7]

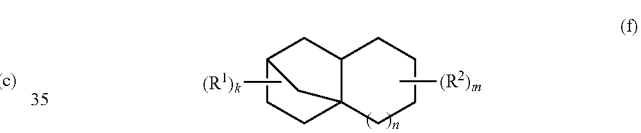
(f)

wherein k, m and n are each an integer of 0 to 6 with the proviso that k+m is an integer of 0 to 6, and $R^1$ and $R^2$ each represent an alkyl group having 1 to 4 carbon atoms or a cycloalkyl group having 5 to 12 carbon atoms, or are taken together to represent an alkylene group having 1 to 7 carbon atoms.

9. A lubricating oil composition characterized in that the lubricating oil composition comprises at least one hydrocarbon compound of any of the above general formulas (a) to (f), and a synthetic traction base oil which is other than said compound and which has an alicyclic structure, and in that the composition has a viscosity at −40° C. of 40 Pa·s or lower and a viscosity index of 80 or higher.

10. A lubricating oil composition as recited in 9 above, wherein the synthetic traction base oil having an alicyclic structure is a hydrocarbon which has 16 to 20 carbon atoms and which is represented by the following general formula (h):

[8]

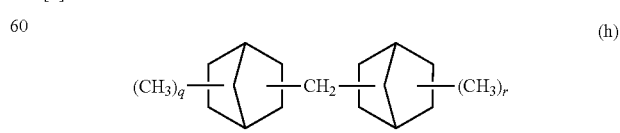
(h)

wherein q is an integer of 1 or 2 and r is an integer of 2 or 3.

11. A lubricating oil composition as recited in 9 above, wherein the synthetic traction base oil having an alicyclic structure is 2,4-dicyclohexyl-2-methylpentane.

12. A lubricating oil composition as recited in 9 above, wherein the synthetic traction base oil having an alicyclic structure is 2,3-dicyclohexyl-2,3-dimethylbutane.

13. A lubricating oil composition comprising a lube base oil or a lubricating oil composition as recited in any one of 1 to 12 above, and, compounded therein, at least one additive selected from the group consisting of an antioxidant, a viscosity index improver, a detergent dispersant, a friction reducing agent, a metal deactivator, a pour point depressant, an abrasion proof agent, an antifoaming agent and an extreme pressure agent.

14. A fluid for traction drive, comprising a lube base oil or a lubricating oil composition as recited in any one of 1 to 13 above.

BEST MODE FOR CARRYING OUT THE INVENTION

The lube base oil and the lubricating oil composition according to the present invention comprise at least one hydrocarbon compound having, as a basic skeleton, a structure represented by any of the general formulas (I) to (VI) shown below and have a viscosity at −40° C. of 40 Pa·s or lower and a viscosity index of 80 or higher. A viscosity of higher than 40 Pa·s at −40° C. is not preferable because the low-temperature startability becomes poor. The viscosity at −40° C. is preferably 35 Pa·s or lower, more preferably 30 Pa·s or lower. The lower limit is not specifically limited but the viscosity is generally 100 mPa·s or higher. A viscosity index of lower than 80 is not preferable because the viscosity is too low at high temperatures to maintain a satisfactory oil film. The viscosity index is preferably 90 or higher. It is further preferred that the traction coefficient at 120° C. be 0.06 or higher, more preferably 0.07 or higher.

[9]

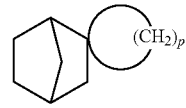 (I)

 (II)

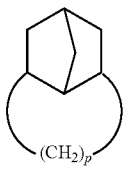 (III)

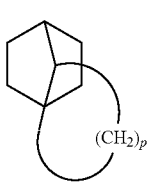 (IV)

-continued

 (V)

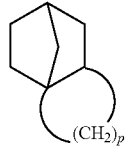 (VI)

In the above formulas, p is an integer of 1 to 10, preferably 2 to 8, with the proviso that, in the formulas (I) and (II), p is not 1. The general formulas (I) to (VI) each include a structure in which the 2- and 6-positions or 3- and 6-positions of the bicyclo[2.2.1]heptane are linked together.

The hydrocarbon compound having, as a basic skeleton, the structure represented by the general formula (I) is preferably a hydrocarbon compound represented by the following general formula (a):

[10]

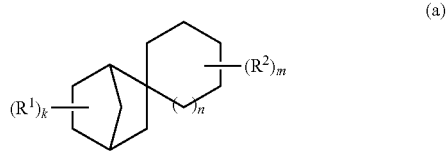 (a)

wherein k, m and n are each an integer of 0 to 6 with the proviso that k+m is an integer of 0 to 6, and $R^1$ and $R^2$ each represent an alkyl group having 1 to 4 carbon atoms or a cycloalkyl group having 5 to 12 carbon atoms, or are taken together to represent an alkylene group having 1 to 7 carbon atoms. The alkyl group having 1 to 4 carbon atoms may be linear or branched and may be, for example, a methyl group, an ethyl group, a n-propyl group, an isopropyl group, a n-butyl group, an isobutyl group, a sec-butyl group or a tert-butyl group. The cycloalkyl group having 5 to 12 carbon atoms may be, for example, a cyclopentyl group, a cyclohexyl group, a cyclooctyl group, a cyclodecyl group, a cyclododecyl group or an adamantyl group and may have an alkyl group or groups on its ring with the proviso that the total number of the carbon atoms is in the range of 5 to 12. The alkylene having 1 to 7 carbon atoms may be, for example, methylene, ethylene, trimethylene or propylene and may have a cross-linked structure on the alkylene with the proviso that the total number of the carbon atoms is in the range of 1 to 7. As specific examples of the above compound, there may be mentioned spiro[bicyclo[2.2.1]heptane-2,1'-cyclopentane], spiro[bicyclo[2.2.1]heptane-2,1'-cyclohexane] and alkyl- or alkylene-substituted derivatives thereof.

The hydrocarbon compound having, as a basic skeleton, the structure represented by the general formula (II) is preferably a hydrocarbon compound represented by the following general formula (b):

[11]

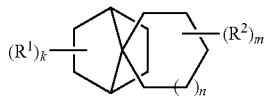
(b)

wherein k, m, n, k+m, $R^1$ and $R^2$ have the same meaning as above. As specific examples of the above compound, there may be mentioned spiro[bicyclo[2.2.1]heptane-7,1'-cyclopentane], spiro[bicyclo[2.2.1]heptane-7,1'-cyclohexane] and alkyl-substituted derivatives thereof.

The hydrocarbon compound having, as a basic skeleton, the structure represented by the general formula (III) is preferably a hydrocarbon compound represented by the following general formula (c):

[12]

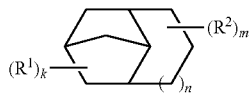
(c)

wherein k, m, n, k+m, $R^1$ and $R^2$ have the same meaning as above. As specific examples of the above compound, there may be mentioned octahydro-1,5-methano-pentalene, octahydro-2,4-methano-indene and alkyl-substituted derivatives thereof.

The hydrocarbon compound having, as a basic skeleton, the structure represented by the general formula (IV) is preferably a hydrocarbon compound represented by the following general formula (d):

[13]

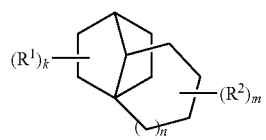
(d)

wherein k, m, n, k+m, $R^1$ and $R^2$ have the same meaning as above. As specific examples of the above compound, there may be mentioned hexahydro-1,3a-ethano-pentalene, octahydro-1,3a-ethano-indene and alkyl-substituted derivatives thereof.

The hydrocarbon compound having, as a basic skeleton, the structure represented by the general formula (V) is preferably a hydrocarbon compound represented by the following general formula (e):

[14]

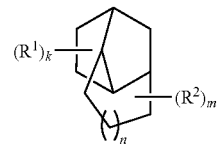
(e)

wherein k, m, n, k+m, $R^1$ and $R^2$ have the same meaning as above. As specific examples of the above compound, there may be mentioned octahydro-1,4-methano-indene, decahydro-1,4-methano-azulene and alkyl-substituted derivatives thereof.

The hydrocarbon compound having, as a basic skeleton, the structure represented by the general formula (VI) is preferably a hydrocarbon compound represented by the following general formula (f):

[15]

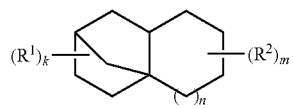
(f)

wherein k, m, n, k+m, $R^1$ and $R^2$ have the same meaning as above. As specific examples of the above compound, there may be mentioned octahydro-3a,6-methano-indene, octahydro-2,4a-methano-naphthalene and alkyl-substituted derivatives thereof.

At least one of the hydrocarbon compounds of the general formulas (a) to (f) may be blended with a synthetic traction base oil, other than the hydrocarbon compounds, having an alicyclic structure.

Illustrative of suitable compounds of the synthetic traction base oil having an alicyclic structure are hydrocarbon compounds having two bridged-rings selected from a bicyclo [2.2.1]heptane ring, a bicyclo[3.2.1]octane ring, a bicyclo [3.3.0]octane ring and a bicyclo[2.2.2]octane ring; 2,4-dicyclohexyl-2-methylpentane; and 2,3-dicyclohexyl-2,3-dimethyl butane.

As the hydrocarbon compound having two bridged-rings, there may be suitably selected from hydrogenation products of dimers of at least one alicyclic compound selected from bicyclo[2.2.1]heptane ring compounds, bicyclo[3.2.1]octane ring compounds, bicyclo[3.3.0]octane ring compounds and bicyclo[2.2.2]octane ring compounds. Above all, further preferred are the hydrogenation products of dimers of bicyclo [2.2.1]heptane ring compounds, i.e., compounds represented by general formula (g):

[16]

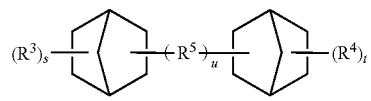
(g)

wherein $R^3$ and $R^4$ each independently represent an alkyl group having 1 to 3 carbon atoms, $R^5$ represents a methylene group, an ethylene group or a trimethylene group, each of which may be substituted with a methyl group or an ethyl group as the side chain, s and t each represent an integer of 0 to 3, and u represents 0 or 1.

Among the compounds represented by the general formula (g), a compound represented by the following general formula (h):

[17]

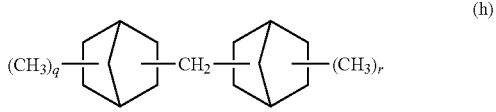

wherein q is an integer of 1 or 2 and r is an integer of 2 or 3, is particularly preferred.

The preferable process for producing the hydrogenation products of dimers of the above alicyclic compounds includes, for example, subjecting a below described olefin, which may be substituted with an alkyl group, to dimerization, hydrogenation and distillation, in this order. Examples of the raw material olefin which may be substituted with an alkyl group include bicyclo[2.2.1]hept-2-ene; an alkenyl-substituted bicyclo[2.2.1]hept-2-ene such as vinyl-substituted or isopropenyl-substituted bicyclo[2.2.1]hept-2-ene; an alkylidene-substituted bicyclo[2.2.1]hept-2-ene such as methylene-substituted, ethylidene-substituted or isopropylidene-substituted bicyclo[2.2.1]hept-2-ene; an alkenyl-substituted bicyclo[2.2.1]heptane such as vinyl-substituted or isopropenyl-substituted bicyclo[2.2.1]heptane; an alkylidene-substituted bicyclo[2.2.1]heptane such as methylene-substituted, ethylidene-substituted or isopropylidene-substituted bicyclo[2.2.1]heptane; bicyclo[3.2.1]octene; an alkenyl-substituted bicyclo[3.2.1]octene such as vinyl-substituted or isopropenyl-substituted bicyclo[3.2.1]octene; an alkylidene-substituted bicyclo[3.2.1]octene such as methylene-substituted, ethylidene-substituted or isopropylidene-substituted bicyclo[3.2.1]octene; an alkenyl-substituted bicyclo[3.2.1]octane such as vinyl-substituted or isopropenyl-substituted bicyclo[3.2.1]octane; an alkylidene-substituted bicyclo[3.2.1]octane such as methylene-substituted, ethylidene-substituted or isopropylidene-substituted bicyclo[3.2.1]octane; bicyclo[3.3.0]octene; an alkenyl-substituted bicyclo[3.3.0]octene such as vinyl-substituted or isopropenyl-substituted bicyclo[3.3.0]octene; an alkylidene-substituted bicyclo[3.3.0]octene such as methylene-substituted, ethylidene-substituted or isopropylidene-substituted bicyclo[3.3.0]octene; an alkenyl-substituted bicyclo[3.3.0]octane such as vinyl-substituted or isopropenyl-substituted bicyclo[3.3.0]octane; an alkylidene-substituted bicyclo[3.3.0]octane such as methylene-substituted, ethylidene-substituted or isopropylidene-substituted bicyclo[3.3.0]octane; bicyclo[2.2.2]octene; an alkenyl-substituted bicyclo[2.2.2]octene such as vinyl-substituted or isopropenyl-substituted bicyclo[2.2.2]octene; an alkylidene-substituted bicyclo[2.2.2]octene such as methylene-substituted, ethylidene-substituted or isopropylidene-substituted bicyclo[2.2.2]octene; an alkenyl-substituted bicyclo[2.2.2]octane such as vinyl-substituted or isopropenyl-substituted bicyclo[2.2.2]octane; and an alkylidene-substituted bicyclo[2.2.2]octane such as methylene-substituted, ethylidene-substituted or isopropylidene-substituted bicyclo[2.2.2]octane.

The hydrogenation products of dimers of bicyclo[2.2.1] heptane cyclic compounds represented by the above general formula (g) or (h) are preferred. Thus, examples of the corresponding raw material olefin include bicyclo[2.2.1]hept-2-ene, 2-methylenebicyclo[2.2.1]heptane, 2-methylbicyclo[2.2.1]hept-2-ene, 2-methylene-3-methylbicyclo[2.2.1] heptane, 3-methylene-2-methylbicyclo[2.2.1]heptane, 2,3-dimethylbicyclo[2.2.1]hept-2-ene, 2-methylene-7-methylbicyclo[2.2.1]heptane, 3-methylene-7-methylbicyclo [2.2.1]heptane, 2,7-dimethylbicyclo-[2.2.1]hept-2-ene, 2-methylene-5-methylbicyclo[2.2.1]heptane, 3-methylene-5-methylbicyclo[2.2.1]heptane, 2,5-dimethylbicyclo[2.2.1] hept-2-ene, 2-methylene-6-methylbicyclo[2.2.1]heptane, 3-methylene-6-methylbicyclo[2.2.1]heptane, 2,6-dimethylbicyclo[2.2.1]hept-2-ene, 2-methylene-1-methylbicyclo [2.2.1]heptane, 3-methylene-1-methylbicyclo[2.2.1]heptane, 1,2-dimethyl bicyclo[2.2.1]hept-2-ene, 2-methylene-4-methylbicyclo[2.2.1]heptane, 3-methylene-4-methyl bicyclo [2.2.1]heptane, 2,4-dimethyl bicyclo[2.2.1]hept-2-ene, 2-methylene-3,7-dimethylbicyclo[2.2.1]heptane, 3-methylene-2,7-dimethylbicyclo[2.2.1]heptane, 2,3,7-trimethylbicyclo[2.2.1]hept-2-ene, 2-methylene-3,6-dimethylbicyclo [2.2.1]heptane, 3-methylene-2,6-dimethylbicyclo[2.2.1] heptane, 2-methylene-3,3-dimethylbicyclo[2.2.1]heptane, 3-methylene-2,2-dimethylbicyclo[2.2.1]heptane, 2,3,6-trimethylbicyclo[2.2.1]hept-2-ene, 2-methylene-3-ethylbicyclo [2.2.1]heptane, 3-methylene-2-ethylbicyclo[2.2.1]heptane and 2-methyl-3-ethylbicyclo[2.2.1]hept-2-ene.

The dimerization described above means not only dimerization of the same olefin but also co-dimerization of a plurality of different olefins. The dimerization of the olefin described above is generally carried out in the presence of a catalyst and, if necessary, by adding a solvent. As the catalyst used for the dimerization, an acid catalyst is generally used. Examples of the catalyst include solid acids such as activated clay, zeolite, montmorillonite and ion exchange resin, mineral acids such as hydrofluoric acid and polyphosphoric acid, organic acids such as triflic acid, Lewis acids such as aluminum chloride, ferric chloride, stannic chloride, boron trifluoride, complexes of boron trifluoride, boron tribromide, aluminum bromide, gallium chloride and gallium bromide, and organoaluminum compounds such as triethylaluminum, diethylaluminum chloride and ethylaluminum dichloride.

The amount of the catalyst is not particularly limited. In general, however, the amount is in the range of 0.1 to 100% by mass based on the olefin used as the raw material. A solvent is not always necessary in the dimerization but may be used for the handling of the raw material olefin and the catalyst during the reaction and for adjusting the progress of the reaction. Examples of the solvent include saturated hydrocarbons such as various pentanes, various hexanes, various octanes, various nonanes and various decanes, alicyclic hydrocarbons such as cyclopentane, cyclohexane, methylcyclohexane and decalin, ether compounds such as diethyl ether and tetrahydrofuran, halogen-containing compounds such as methylene chloride and dichloroethane, and nitro compounds such as nitromethane and nitrobenzene.

The dimerization is conducted in the presence of the above catalyst. The reaction temperature is generally in the range of –70 to 200° C. The reaction conditions are properly selected according to the kind of the catalyst and additives in the above temperature range. The reaction pressure is generally the atmospheric pressure and the reaction time is generally in the range of 0.5 to 10 hours.

The dimer of the raw material olefin thus obtained is then hydrogenated to obtain the desired hydrogenation product of the dimer. If desired, the hydrogenation may be performed for properly mixed dimmers separately dimerized using separate raw material olefins.

The hydrogenation may be also carried out in the presence of a catalyst. As the catalyst, there may be mentioned a hydrogenation catalyst such as nickel, ruthenium, palladium, platinum, rhodium or iridium. The catalyst is generally used in an amount of 0.1 to 100% by mass based on the dimerization product.

Similarly to the above-described dimerization, the hydrogenation can proceed without a solvent although a solvent may be used. Examples of the solvent include saturated hydrocarbons such as various pentanes, various hexanes, various octanes, various nonanes and various decanes, and alicyclic hydrocarbons such as cyclopentane, cyclohexane, methylcyclohexane and decalin.

The reaction temperature may be generally from 20 to 300° C. and the reaction pressure is from the atmospheric pressure to 20 MPa. The reaction time is generally in the range of 1 to 10 hours. The hydrogenation product thus obtained may be mixed with a hydrogenation product formed from separate raw material olefin in separate process.

In the present invention, when the hydrocarbon compound having as its basic skeleton a structure represented by any of the general formulas (I) to (VI) is used as a blend with the synthetic traction base oil having an alicyclic structure, the mixing proportion is not indiscriminately determined. The amount is determined in consideration of the high-temperature traction coefficients, low-temperature viscosities and viscosity indexes of the hydrocarbon compound and synthetic traction base oil. Generally, however, the mixing proportion of the hydrocarbon compound is in the range of 1 to 60% by mass. Within such a range, the improvement attained by the hydrocarbon compound is significant and a reduction of the high-temperature traction coefficient is small. Preferably, the mixing proportion is 2 to 50% by mass. In any case, it is essential that the hydrocarbon compound and the synthetic traction base oil should be mixed in a proportion so as to provide a viscosity at −40° C. of 40 Pa·s or lower and a viscosity index of 80 or higher.

The lube base oil and lubricating oil composition of the present invention may be used not only as a traction drive fluid but also as a lubricating composition by being compounded with various additives depending upon the object of use. Namely, though the lube base oil and lubricating oil composition of the present invention may be used as such as a lubricating oil, they may be compounded with the below-described additives selected according to the object of use to form a lubricating oil composition and may be preferably used as a lubricating oil suitable for the intended use.

As the additives, various additives including known additives may be used. For example, there may be mentioned an antioxidant such as an amine compound, e.g. alkylated diphenylamine and phenyl-α-naphthylamine, or a phenol compound, e.g. 2,6-di-t-butylphenol or 4,4'-methylene-bis(2,6-di-t-butylphenol); a viscosity index improver such as a polymethylmethacrylate-based, a polyisobutylene-based, an ethylene-propylene copolymer-based, a styrene-isoprene copolymer-based or a styrene-butadiene hydrogenated copolymer-based viscosity index improver; a detergent such as a metal-based detergent dispersant, e.g. an alkaline earth metal sulfonate, an alkaline earth metal phenate, an alkaline earth metal salicylate or an alkaline earth metal phosphonate, or a non-ash dispersant, e.g. alkenyl succinimide, benzylamine, alkylpolyamine or alkenyl succinate; a friction reducing agent such as an aliphatic alcohol, a fatty acid, a fatty acid ester, an aliphatic amine, a fatty amine salt or fatty acid amide; a metal deactivator such as benzotriazole, thiadiazole or alkenyl succinate; a pour point depressant such as polyalkylmethacrylate or polyalkylstyrene; an abrasion proof agent such as an organomolybdenum compound, e.g. MoDTP or MoDTC, an organozinc compound, e.g. ZnDTP or an organoboron compound, e.g. alkylmercaptyl borate, or a solid lubricant abrasion proof agent, e.g. graphite, molybdenum disulfide, antimony sulfide, a boron compound or polytetrafluoroethylene; an antifoaming agent such as dimethylpolysiloxane or polyacrylate; and an extreme pressure agent such as sulfurized fat, diphenyl sulfide, methyl trichlorostearate or chlorinated naphthalene.

The lube base oil of the present invention may be utilized, for example, as a traction drive fluid, a hydraulic fluid, an automatic transmission fluid, a manual transmission fluid, a damper fluid, a gear fluid, a fluid bearing oil, an antifriction bearing fluid, an oil impregnated bearing fluid, a sliding surface oil or a refrigerator oil.

EXAMPLES

The present invention will be next described in detail by way of Examples. However, the present invention is not restricted to these Examples in any way.

Comparative Example 1

In a 500 mL four-necked flask equipped with a reflux condenser, a stirrer and a thermometer, 4 g of activated clay (GALEON EARTH NS, manufactured by Mizusawa Industrial Chemicals, Ltd), 10 g of diethylene glycol monoethyl ether and 200 g of α-methylstyrene were placed. The resultant mixture was heated at a reaction temperature of 105° C. and stirred for 4 hours. After the reaction was completed, the produced liquid was analyzed by gas chromatography. It was found that the conversion was 70%, the selectivity to the desired linear dimer of α-methylstyrene was 95%, the selectivity to the by-product cyclic dimer of α-methylstyrene was 1%, and the selectivity to higher boiling point substances such as trimers was 4%. The obtained reaction mixture was hydrogenated (hydrogen pressure: 2.94 MPa; reaction temperature: 200° C.; reaction time: 3 hours) in a 1 L autoclave containing 6 g of a nickel/diatomaceous earth hydrogenation catalyst (N-113, manufactured by Nikki Chemical Co., Ltd.). After completion of the reaction, the catalyst was removed by filtration. The filtrate was distilled under reduced pressure to obtain 125 g of the hydrogenation product of the linear dimer of α-methylstyrene, i.e., 2,4-dicyclohexyl-2-methylpentane (Fluid A), having a purity of 99%. The results of the measurements of the properties and the traction coefficient of the hydrogenation product of the dimer are shown in Table 1.

Comparative Example 2

In a 2 L stainless steel autoclave, 561 g (8 moles) of crotonaldehyde and 352 g (2.67 moles) of dicyclopentadiene were placed and reacted at 170° C. for 3 hours. After cooling, 18 g of a Raney nickel catalyst (M-300T, manufactured by Kawaken Fine Chemicals Co., Ltd.) was added, and the mixture was subjected to hydrogenation at a reaction temperature of 150° C. and a hydrogen pressure of 0.88 MPa for 4 hours. After cooling, the catalyst was removed by filtration. The filtrate was distilled under reduced pressure to obtain 565 g of a fraction of 105° C./2.67 kPa. The fraction was identified as 2-hydroxymethyl-3-methylbicyclo[2.2.1]heptane from the analysis by the mass spectrum and the nuclear magnetic resonance spectrum thereof.

Next, in an atmospheric reaction tube of a flow type made of quartz and having an outer diameter of 20 mm and a length of 500 mm, 20 g of γ-alumina (N612, manufactured by Nikki Chemical Co., Ltd.) was placed. The dehydration was conducted at a reaction temperature of 285° C. and a weight hourly space velocity (WHSV) of 1.1 hr$^{-1}$, so that a dehydration product of 2-hydroxymethyl-3-methylbicyclo[2.2.1] heptane containing 2-methylene-3-methylbicyclo[2.2.1]heptane and 2,3-dimethylbicyclo[2.2.1]hept-2-ene was obtained in an amount of 490 g.

In a 1 L four-necked flask, 10 g of boron trifluoride-diethyl etherate and 490 g of the olefin compound obtained above were placed. The dimerization was conducted for 5 hours with stirring at 10° C. The resultant reaction mixture was washed with a dilute aqueous NaOH solution and with a saturated aqueous sodium chloride solution and was hydrogenated (hydrogen pressure: 2.94 MPa, reaction temperature: 250° C., reaction time: 5 hours) in a 1 L autoclave containing 15 g of a nickel/diatomaceous earth hydrogenation catalyst (N-113, manufactured by Nikki Chemical Co., Ltd.). After completion of the reaction, the catalyst was removed by filtration. The filtrate was distilled under reduced pressure to obtain 340 g of the desired hydrogenation product (Fluid B) of the dimer. The results of the measurements of the properties and the traction coefficient of the desired hydrogenation product of the dimer are shown in Table 1.

Example 1

In a 2 L autoclave, 1,000 g of longifolene (manufactured by Yasuhara Chemical Co., Ltd.) and 30 g of a nickel/diatomaceous earth hydrogenation catalyst (N-113, manufactured by Nikki Chemical Co., Ltd.) were placed and the hydrogenation thereof was carried out at a hydrogen pressure of 3 MPa and a reaction temperature of 250° C. for 4 hours. After completion of the reaction, the catalyst was removed by filtration. The filtrate was subjected to fractional distillation to obtain 500 g of the desired hydrogenated product (Fluid 1) of longifolene having the following structural formula:

[18]

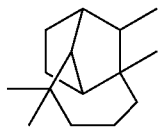

The results of the measurements of the properties and the traction coefficient are shown in Table 1.

Example 2

Fluid 1 of Example 1 was blended with Fluid A of Comparative Example 1 so that the amount of Fluid 1 was 50% by mass of the blend. The results of the measurements of the properties and the traction coefficient are shown in Table 1.

Example 3

Fluid 1 of Example 1 was blended with Fluid B of Comparative Example 2 so that the amount of the Fluid 1 was 20% by mass of the blend. The results of the measurements of the properties and the traction coefficient are shown in Table 1.

Example 4

In a 5 L four-necked flask, 1,000 g of longifolene (manufactured by Yasuhara Chemical Co., Ltd.) and 500 mL of acetic acid were placed, to which 500 mL of boron trifluoride-diethyl etherate was added dropwise at 20° C. over 4 hours with stirring to carry out the isomerization. The reaction mixture was washed with ice water, a saturated aqueous sodium hydrogen carbonate solution and a saturated aqueous sodium chloride solution, and then refined by distillation. Thereafter, the refined product was placed in a 2 L autoclave together with 18 g of a palladium-carbon hydrogenation catalyst and subjected to hydrogenation (hydrogen pressure: 3 MPa, reaction temperature: 100° C., reaction time: 3 hours). After completion of the reaction, the catalyst was removed by filtration. The filtrate was subjected to fractional distillation to obtain 600 g of the desired isomerized and hydrogenated product (Fluid 2) of longifolene having the following structural formula:

[19]

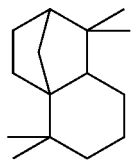

The results of the measurements of the properties and the traction coefficient are shown in Table 1.

Example 5

Fluid 2 of Example 4 was blended with Fluid A of Comparative Example 1 so that the amount of Fluid 2 was 50% by mass of the blend. The results of the measurements of the properties and the traction coefficient are shown in Table 1.

Example 6

Fluid 2 of Example 4 was blended with Fluid B of Comparative Example 2 so that the amount of the Fluid 2 was 20% by mass of the blend. The results of the measurements of the properties and the traction coefficient are shown in Table 1.

Comparative Example 3

In a 2 L stainless steel autoclave, 561 g (8 moles) of crotonaldehyde and 352 g (2.67 moles) of dicyclopentadiene were placed and reacted at 170° C. for 3 hours. After cooling, 18 g of a Raney nickel catalyst (M-300T, manufactured by Kawaken Fine Chemicals Co., Ltd.) was added, and the mixture was subjected to hydrogenation at a reaction temperature of 150° C. and a hydrogen pressure of 0.89 MPa for 4 hours. After cooling, the catalyst was removed by filtration. The filtrate was distilled under reduced pressure to obtain 565 g of a fraction of 105° C./2.67 kPa. The fraction was identified as 2-hydroxymethyl-3-methylbicyclo[2.2.1]heptane from the analysis by the mass spectrum and the nuclear magnetic resonance spectrum thereof.

Next, in an atmospheric reaction tube of a flow type made of quartz and having an outer diameter of 20 mm and a length of 500 mm, 20 g of γ-alumina (N612, manufactured by Nikki Chemical Co., Ltd.) was placed. The dehydration was conducted at a reaction temperature of 285° C. and a weight hourly space velocity (WHSV) of 1.1 hr$^{-1}$, so that a dehydration product of 2-hydroxymethyl-3-methylbicyclo[2.2.1] heptane containing 2-methylene-3-methylbicyclo[2.2.1]heptane and 2,3-dimethylbicyclo[2.2.1]hept-2-ene was obtained in an amount of 490 g.

In a 5 L four-necked flask, 400 g of n-heptane and 200 g of boron trifluoride-diethyl etherate were placed, to which a mixture of 980 g of the olefin compound obtained above and 900 g of diisobutylene was added dropwise at 10° C. over 6 hours with stirring. The resultant reaction mixture was washed with a dilute aqueous NaOH solution and with a saturated aqueous sodium chloride solution and then distilled under reduced pressure to obtain 630 g of a fraction having a boiling point of 130-133° C./1.06 kPa. The analysis revealed that the fraction was a codimer of the raw material olefins. The codimer was placed in a 2 L autoclave together with 19 g of a nickel/diatomaceous earth hydrogenation catalyst (N-113, manufactured by Nikki Chemical Co., Ltd.) and was hydrogenated (hydrogen pressure: 2.94 MPa, reaction temperature: 250° C., reaction time: 5 hours). After completion of the reaction, the catalyst was removed by filtration to obtain 620 g of the desired hydrogenation product (Fluid C) of the dimer. The results of the measurements of the properties and the traction coefficient of the desired hydrogenation product of the dimer are shown in Table 1, from which it will be appreciated that the traction coefficient is low.

Comparative Example 4

Fluid C of Comparative Example 3 was blended with Fluid A of Comparative Example 1 so that the amount of Fluid C was 50% by mass of the blend. The results of the measurements of the properties and the traction coefficient are shown in Table 1. From the comparison with Example 2 or 6, it will be appreciated that the viscosity at a high temperature (100° C.) is low though the viscosity at a low temperature (−40° C.) is comparable. Namely, the viscosity index is low and traction coefficient is low, as well.

Comparative Example 5

In a 3 L four-necked flask were placed 820 g of benzene and 53 g of concentrated sulfuric acid, to which 428 g of the dehydration product of 2-hydroxymethyl-3-methylbicyclo[2.2.1]heptane containing 2-methylene-3-methylbicyclo[2.2.1]heptane and 2,3-dimethylbicyclo[2.2.1]hept-2-ene as main ingredients was added dropwise over 3 hours to perform alkylation. The reaction mixture was washed with a dilute aqueous NaOH solution and with a saturated aqueous sodium chloride solution. After the removal of unreacted benzene by distillation, the washed mixture was placed in a 2 L autoclave together with 18 g of a nickel/diatomaceous earth hydrogenation catalyst (N-113, manufactured by Nikki Chemical Co., Ltd.) and was hydrogenated (hydrogen pressure: 2 MPa, reaction temperature: 250° C., reaction time: 8 hours). After completion of the reaction, the catalyst was removed by filtration and the filtrate was distilled under reduced pressure to obtain 210 g of the desired cyclohexyl-dimethylbicyclo[2.2.1]heptane (Fluid D). The results of the measurements of the properties and the traction coefficient are shown in Table 1, from which it will be appreciated that the traction coefficient is low.

Comparative Example 6

Fluid D of Comparative Example 5 was blended with Fluid A of Comparative Example 1 so that the amount of Fluid D was 50% by mass of the blend. The results of the measurements of the properties and the traction coefficient are shown in Table 1. From the comparison with Example 3 shown in Table 1, it will be appreciated that the viscosity at a high temperature (100° C.) is low though the viscosity at a low temperature (−40° C.) is comparable. Namely, the viscosity index is low and traction coefficient is low, as well.

TABLE 1-1

|  | Comparative Example 1 Fluid A | Comparative Example 2 Fluid B | Example 1 Fluid 1 | Example 2 Fluid 1 + Fluid A | Example 3 Fluid 1 + Fluid B | Example 4 Fluid 2 |
|---|---|---|---|---|---|---|
| Kinematic viscosity @ 40° C. mm$^2$/s | 20.23 | 17.32 | 8.347 | 12.68 | 14.70 | 6.425 |
| Kinematic viscosity @ 100° C. mm$^2$/s | 3.572 | 3.578 | 2.518 | 2.986 | 3.315 | 2.198 |
| Viscosity index | 13 | 77 | 137 | 81 | 90 | 172 |
| Pour point ° C. | −42.5> | −50> | −50> | −50> | −50> | −50> |
| Low temperature viscosity @ −40° C. Pa•s | 256 | 55 | 1> | 4 | 15 | 1> |
| Density g/cm$^3$ | 0.9009 | 0.9544 | 0.9257 | 0.9131 | 0.9485 | 0.9343 |
| Traction coefficient @ 120° C. | 0.082 | 0.086 | 0.075 | 0.079 | 0.085 | 0.061 |
| Remarks |  |  |  | Fluid 1: 50% by mass | Fluid 1: 20% by mass |  |

TABLE 1-2

|  | Example 5 Fluid 2 + Fluid A | Example 6 Fluid 2 + Fluid B | Comparative Example 3 Fluid C | Comparative Example 4 Fluid A + Fluid C | Comparative Example 5 Fluid D | Comparative Example 6 Fluid A + Fluid D |
|---|---|---|---|---|---|---|
| Kinematic viscosity @ 40° C. mm$^2$/s | 10.93 | 13.78 | 6.535 | 10.82 | 7.034 | 11.49 |
| Kinematic viscosity @ 100° C. mm$^2$/s | 2.778 | 3.212 | 2.038 | 0.639 | 2.002 | 2.634 |
| Viscosity index | 93 | 95 | 103 | 64 | 61 | 38 |
| Pour point ° C. | −50> | −50> | −50> | −50> | −50> | −50> |
| Low temperature viscosity @ −40° C. Pa•s | 2 | 3 | 1> | 3 | 3.5 | 15 |
| Density g/cm$^3$ | 0.9173 | 0.9503 | 0.8713 | 0.8859 | 0.9242 | 0.9124 |
| Traction coefficient @ 120° C. | 0.072 | 0.081 | 0.057 | 0.069 | 0.074 | 0.078 |

TABLE 1-2-continued

|  | Example 5<br>Fluid 2 + Fluid A | Example 6<br>Fluid 2 + Fluid B | Comparative<br>Example 3<br>Fluid C | Comparative<br>Example 4<br>Fluid A + Fluid C | Comparative<br>Example 5<br>Fluid D | Comparative<br>Example 6<br>Fluid A + Fluid D |
|---|---|---|---|---|---|---|
| Remarks | Fluid 2: 50%<br>by mass | Fluid 2: 20%<br>by mass |  | Fluid C: 50%<br>by mass |  | Fluid D: 50%<br>by mass |

The measurement of the traction coefficient at 120° C. in the above Examples and Comparative Examples was conducted using a two-cylinder friction tester. Thus, one of the two cylinders having the same size and in contact with each other (diameter: 52 mm, thickness: 6 mm, driven cylinder: drum-shape with a radius of curvature of 10 mm, driving cylinder: flat shape without crowning) was rotated at a constant speed, while the other was rotated at continuously varying speed. A load of 98.0 N was applied with a weight to the point at which the two cylinders were in contact with each other. The tangential force, i.e., the traction force, generated between the two cylinders was measured to determine the traction coefficient. The cylinders were made of mirror finished bearing steel SUJ-2. The average circumferential speed was 6.8 m/s and the maximum Hertz contact pressure was 1.23 GPa. For the measurement of the traction coefficient at a fluid temperature (oil temperature) of 120° C., the oil tank was heated with a heater to raise the oil temperature from 40° C. to 140° C. The traction coefficient at a slipping ratio of 5% was measured.

Example 7

In a 2 L four-necked flask, 1,000 g of longifolene (manufactured by Yasuhara Chemical Co., Ltd.) and 100 g of bromoacetic acid were placed and reacted at 170° C. for 18 hours. The reaction mixture was washed with a saturated aqueous sodium hydrogen carbonate solution and with water and then refined by distillation. Thereafter, the refined product was placed in a 2 L autoclave together with 18 g of a palladium-carbon hydrogenation catalyst and subjected to hydrogenation (hydrogen pressure: 6 MPa, reaction temperature: 100° C., reaction time: 2 hours). After completion of the reaction, the catalyst was removed by filtration. The filtrate was subjected to fractional distillation to obtain 200 g of the desired 4-isopropyl-1,7a-dimethyl-octahydro-1,4-methano-indene (Fluid 3). The results of the measurements of the properties and the traction coefficient are shown in Table 1.

Example 8

Fluid 3 of Example 7 was blended with Fluid B of Comparative Example 2 so that the amount of the Fluid 3 was 20% by mass of the blend. The results of the measurements of the properties and the traction coefficient are shown in Table 1.

Example 9

In a 2 L four-necked flask, 1,000 g of longifolene (manufactured by Yasuhara Chemical Co., Ltd.) and 100 g of bromoacetic acid were placed and reacted at 170° C. for 4 hours. The reaction mixture was washed with a saturated aqueous sodium hydrogen carbonate solution and with water and then refined by distillation. Thereafter, the refined product was mixed to 4 L of methylene chloride and 2 L of 0.5 N aqueous sodium hydrogen carbonate solution, to which 900 g of 3-chloroperbenzoic acid (reagent manufactured by Kanto Chemical Co., Ltd., purity: 65%) was slowly added at a temperature of 10° C. or less. After completion of the reaction, the reaction mixture was washed with 1 N aqueous sodium hydroxide solution and with water and then purified by silica gel chromatography to obtain 160 g of desired tricycle[$2.2.1.0^{2,6}$]heptane derivative (Fluid 4). The results of the measurements of the properties and the traction coefficient are shown in Table 1.

Example 10

Fluid 4 of Example 9 was blended with Fluid B of Comparative Example 2 so that the amount of the Fluid 4 was 20% by mass of the blend. The results of the measurements of the properties and the traction coefficient are shown in Table 1.

Example 11

In a 1 L autoclave, 300 g of the tricyclo[$2.2.1.0^{26}$-]heptane derivative (Fluid 4) of Example 9 was charged together with 9 g of a palladium-carbon hydrogenation catalyst and subjected to hydrogenation (hydrogen pressure: 6 MPa, reaction temperature: 200° C., reaction time: 4 hours). After completion of the reaction, the catalyst was removed by filtration. The filtrate was distilled under reduced pressure to obtain 290 g of desired 1,5,5,8a-tetramethyl-decahydro-1,4-methano-azulene (Fluid 5). The results of the measurements of the properties and the traction coefficient are shown in Table 1.

Example 12

Fluid 5 of Example 11 was blended with Fluid B of Comparative Example 2 so that the amount of the Fluid 5 was 20% by mass of the blend. The results of the measurements of the properties and the traction coefficient are shown in Table 1.

Example 13

In a 5 L four-necked flask, 200 g of longifolene (manufactured by Yasuhara Chemical Co., Ltd.) and 2.5 L of 1.0 N hexane solution of diethylzinc were placed, to which 350 mL of diiodomethane was slowly added dropwise at room temperature. After completion of the reaction, the reaction mixture was washed with saturated aqueous ammonium chloride solution and with water and then purified by distillation to obtain 189 g of desired spiro[4,8,8-trimethyl-decahydro-1,4-methano-azulene-9,1'-cyclopropane] (Fluid 6). The results of the measurements of the properties and the traction coefficient are shown in Table 1.

Example 14

Fluid 6 of Example 13 was blended with Fluid B of Comparative Example 2 so that the amount of the Fluid 6 was 50% by mass of the blend. The results of the measurements of the properties and the traction coefficient are shown in Table 1.

Example 15

In a 3 L four-necked flask was placed 680 mL of diethyl ether, to which 360 g of concentrated sulfuric acid and 920 g of β-caryophyllene (manufactured by Tokyo Kasei Kogyo Co., Ltd.) were slowly added dropwise at 0° C. After 20 hours, the reaction mixture was washed with aqueous sodium hydroxide solution and collected by steam distillation. This was then separated by silica gel chromatography. The fractional distillation of the product gave 100 g of an isomerization product of β-caryophyllene. This was diluted with 300 mL of hexane and charged in a 1 L autoclave together with 9 g of a palladium-carbon hydrogenation catalyst and subjected to hydrogenation (hydrogen pressure: 6 MPa, reaction temperature: 100° C., reaction time: 1 hour). After completion of the reaction, the catalyst was removed by filtration. The filtrate was distilled under reduced pressure to obtain 95 g of desired 4,7a,9,9-tetramethyl-octahydro-1,3a-ethano-indene (Fluid 7). The results of the measurements of the properties and the traction coefficient are shown in Table 1.

Example 16

Fluid 7 of Example 15 was blended with Fluid B of Comparative Example 2 so that the amount of the Fluid 7 was 20% by mass of the blend. The results of the measurements of the properties and the traction coefficient are shown in Table 1.

Example 17

In a 2 L four-necked flask, 500 g of longifolene (manufactured by Yasuhara Chemical Co., Ltd.) and 250 mL of acetic acid were placed, to which 250 mL of boron trifluoride-diethyl etherate was added dropwise at 20° C. over 4 hours with stirring to carry out the isomerization. The reaction mixture was washed with ice water, a saturated aqueous sodium hydrogen carbonate solution and a saturated aqueous sodium chloride solution, and then refined by distillation. Thereafter, the refined product was mixed to 1,800 mL of methylene chloride and 900 mL of 0.5 N aqueous sodium hydrogen carbonate solution, to which 400 g of 3-chloroperbenzoic acid was slowly added at a temperature of 10° C. or less. After completion of the reaction, the reaction mixture was washed with 1 N aqueous sodium hydroxide solution and with water and concentrated in vacuo. The thus obtained crude product was dissolved in 3 L of toluene, to which 260 mL of boron trifluoride-diethyl etherate was slowly added dropwise at 5° C. or less. After completion of the reaction, the reaction mixture was washed with water and then refined by distillation to obtain 270 g of 1,1,5,5-tetramethyl-hexahydro-2,4a-methano-naphthalene-8-one. This was added dropwise at 5° C. or less to 640 mL of 2.1 N diethyl ether solution of methyllithium to carry out the alkylation. After completion of the reaction, the reaction mixture was washed with saturated aqueous ammonium chloride solution and with water and, then, charged in a 1 L autoclave together with 30 g of a nickel/diatomaceous earth hydrogenation catalyst (N-113, manufactured by Nikki Chemical Co., Ltd.) and was hydrogenated (hydrogen pressure: 6 MPa, reaction temperature: 250° C., reaction time: 6 hours).

After completion of the reaction, the catalyst was removed by filtration and the filtrate was distilled under a reduced pressure to obtain 240 g of desired 1,1,5,5,8-pentamethyl-octahydro-2,4a-methano-naphthalene (Fluid 8). The results of the measurements of the properties and the traction coefficient are shown in Table 1.

Example 18

Fluid 8 of Example 16 was blended with Fluid B of Comparative Example 2 so that the amount of the Fluid 8 was 20% by mass of the blend. The results of the measurements of the properties and the traction coefficient are shown in Table 1.

Example 19

In a 2 L four-necked flask equipped with a reflux condenser, a stirrer, a dropping funnel and a thermometer, 600 mL of hexane and 195 g of sodium amide were placed and the resulting suspension was heated and refluxed. To the suspension, a solution of 304 g of camphor and 628 g of 1,4-dibromobutane dissolved in 600 mL of hexane was added dropwise over 1 hour. Thereafter, the mixture was heated and refluxed for 13 hours.

The reaction product was poured into a 10% aqueous sulfuric acid solution and extracted with ethyl acetate. The organic layer was dried, concentrated and then distilled under reduced pressure to obtain 326 g of spiro[1,7,7-trimethyl-bicyclo[2.2.1]heptane-2-one-3,1'-cyclopentane].

In a 2 L four-necked flask equipped with a reflux condenser, a stirrer, a dropping funnel and a thermometer, 206 g of spiro[1,7,7-trimethyl-bicyclo[2.2.1]heptane-2-one-3,1'-cyclopentane] and 600 mL of diethyl ether were placed, to which 600 mL of 2.1 N diethyl ether solution of methyllithium was added dropwise over 1 hour and the reaction mixture was reacted at room temperature for 6 hours.

The reaction product was poured into a 10% aqueous sulfuric acid solution and extracted with ethyl acetate. The organic layer was dried and concentrated. The residue was then placed in a 2 L eggplant type flask equipped with a reflux condenser and Dean-Stark trap, to which 1 L of toluene and 1.8 g of p-toluenesulfonic acid were added. The resulting mixture was then heated and refluxed for 2 hours while removing the water produced.

After cooling, the thus obtained mixture was washed with saturated aqueous sodium hydrogen carbonate solution. The organic layer was then dried and concentrated to obtain 204 g of spiro[1,7,7-trimethyl-2-methylene-bicyclo[2.2.1]heptane-3,1'-cyclopentane]. This was dissolved in hexane to obtain 600 mL of a solution. The solution was placed in a 2 L autoclave together with 18 g of 10% palladium-carbon hydrogenation catalyst and subjected to hydrogenation (hydrogen pressure: 4 MPa, reaction temperature: 40° C., reaction time: 6 hours). The reaction mixture was filtered and the filtrate was concentrated and distilled under reduced pressure to obtain 190 g of spiro[1,2,7,7-tetramethyl-bicyclo[2.2.1]heptane-3,1'-cyclopentane] (Fluid 9). The results of the measurements of the properties and the traction coefficient are shown in Table 1.

Example 20

Fluid 9 of Example 19 was blended with Fluid B of Comparative Example 2 so that the amount of the Fluid 9 was 20% by mass of the blend. The results of the measurements of the properties and the traction coefficient are shown in Table 1.

Example 21

The procedures of Example 19 were conducted in the same manner as described in Example 19 except that 690 g of 1,5-dibromopentane was used in lieu of 628 g of 1,4-dibromobutane to obtain 80 g of spiro[1,2,7,7-tetramethyl-bicyclo[2.2.1]heptane-2-one-3,1'-cyclohexane] (Fluid 10). The results of the measurements of the properties and the traction coefficient are shown in Table 1.

Example 22

Fluid 10 of Example 21 was blended with Fluid B of Comparative Example 2 so that the amount of the Fluid 10 was 30% by mass of the blend. The results of the measurements of the properties and the traction coefficient are shown in Table 1.

Example 23

In a 2 L four-necked flask equipped with a reflux condenser, a stirrer and a thermometer, 13.0 g of cobalt iodide dihydrate was placed and heated under reduced pressure to remove the water. This was then suspended in 700 mL of dichloromethane, to which 9.83 g of triphenylphosphine, 138 g of 2,5-norbornadiene, 153 g of phenylacetylene and 24.5 g of zinc were added. The mixture was then reacted at room temperature for 6 hours. The reaction mixture was filtered, concentrated and refined by silica gel chromatography (developing solvent: hexane). The product was diluted with 600 mL of hexane and charged in a 1 L autoclave together with 18 g of a 5% ruthenium-carbon hydrogenation catalyst and subjected to hydrogenation (hydrogen pressure: 4 MPa, reaction temperature: 70° C., reaction time: 2.5 hours).

After the completion of the reaction, the reaction mixture was filtered and the filtrate was concentrated and distilled under reduced pressure to obtain 230 g of 8-cyclohexyl-tetracyclo[4.3.0.0$^{2,4}$.0$^{3,7}$]nonane (Fluid 11). The results of the measurements of the properties and the traction coefficient are shown in Table 1.

Example 24

Fluid 11 of Example 23 was blended with Fluid B of Comparative Example 2 so that the amount of the Fluid 11 was 30% by mass of the blend. The results of the measurements of the properties and the traction coefficient are shown in Table 1.

Example 25

In 200 mL of hexane, 100 g of 8-cyclohexyl-tetracyclo[4.3.0.0$^{2,4}$.0$^{3,7}$]nonane (Fluid 11) of Example 23 was dissolved. The solution was charged in a 1 L autoclave together with 9.0 g of 10% palladium-carbon hydrogenation catalyst and subjected to hydrogenation (hydrogen pressure: 6 MPa, reaction temperature: 200° C., reaction time: 10 hours).

After the completion of the reaction, the reaction mixture was filtered and the filtrate was concentrated and distilled under reduced pressure to obtain 87 g of a mixture (Fluid 12) of three compounds, 2-cyclohexyl-octahydro-1,5-methano-pentalene, 2-cyclohexyl-octahydro-1,4-methano-pentalene and 3-cyclohexyl-octahydro-1,4-methano-pentalene. The results of the measurements of the properties and the traction coefficient are shown in Table 1.

Example 26

Fluid 12 of Example 25 was blended with Fluid B of Comparative Example 2 so that the amount of the Fluid 12 was 50% by mass of the blend. The results of the measurements of the properties and the traction coefficient are shown in Table 1.

Example 27

In a 2 L four-necked flask equipped with a reflux condenser, a stirrer and a thermometer, 13.1 g of cobalt iodide dihydrate was placed and heated under reduced pressure to remove the water. This was then suspended in 520 mL of dichloroethane, to which 13.2 g of 1,2-bis(diphenylphosphino)ethane, 276 g of 2,5-norbornadiene and 24.6 g of zinc were added. The mixture was then heated and refluxed for 6 hours. The reaction mixture was filtered, concentrated and distilled under reduced pressure to obtain 128 g of hexacyclo[9.2.1.0$^{2,10}$.0$^{3,8}$.0$^{4,6}$.0$^{5,9}$]-12-tetradecene. The product was dissolved in 300 mL of hexane and charged in a 1 L autoclave together with 9.0 g of 10% palladium-carbon hydrogenation catalyst and subjected to hydrogenation (hydrogen pressure: 3 MPa, reaction temperature: room temperature, reaction time: 30 minutes). The catalyst was filtered and the filtrate was concentrated and distilled under reduced pressure to obtain 120 g of hexacyclo[9.2.1.0$^{2,10}$.0$^{3,8}$.0$^{4,6}$.0$^{5,9}$]tetradecane (Fluid 13). The results of the measurements of the properties and the traction coefficient are shown in Table 1.

Example 28

Fluid 13 of Example 27 was blended with Fluid B of Comparative Example 2 so that the amount of the Fluid 13 was 30% by mass of the blend. The results of the measurements of the properties and the traction coefficient are shown in Table 1.

Example 29

130 g of hexacyclo[9.2.1.0$^{2,10}$.0$^{3,8}$.0$^{4,6}$.0$^{5,9}$]tetradecane (Fluid 13) of Example 27 was diluted with hexane to a 600 mL solution. The solution was charged in a 2 L autoclave together with 18.0 g of 10% palladium-carbon hydrogenation catalyst and subjected to hydrogenation (hydrogen pressure: 4 MPa, reaction-temperature: 200° C., reaction time: 1 hour).

The catalyst was filtered and the filtrate was concentrated and distilled under reduced pressure to obtain 105 g of a mixture (Fluid 14) of pentacyclo[8.2.1.1$^{5,8}$.0$^{2,9}$.0$^{3,7}$]tetradecane and hexacyclo[9.2.1.0$^{2,10}$.0$^{3,8}$.0$^{5,9}$]tetradecane. The results of the measurements of the properties and the traction coefficient are shown in Table 1.

Example 30

Fluid 14 of Example 29 was blended with Fluid B of Comparative Example 2 so that the amount of the Fluid 14 was 30% by mass of the blend. The results of the measurements of the properties and the traction coefficient are shown in Table 1.

Example 31

In a 2 L four-necked flask equipped with a reflux condenser, a stirrer and a thermometer, 8.7 g of cobalt iodide dihydrate was placed and heated under reduced pressure to remove the water. This was then suspended in 180 mL of dichloroethane, to which 6.55 g of triphenylphosphine, 184 g of 2,5-norbornadiene and 16.4 g of zinc were added. The mixture was then heated and refluxed for 1 hour. The reaction mixture was filtered, concentrated and subjected to silica gel column chromatography to collect a hexane fraction. This was dissolved in 600 mL of hexane and charged in a 2 L autoclave together with 9.0 g of 10% palladium-carbon hydrogenation catalyst and subjected to hydrogenation (hydrogen pressure: 4 MPa, reaction temperature: 200° C., reaction time: 4.5 hours).

The catalyst was filtered and the filtrate was concentrated and distilled under reduced pressure to obtain 132 g of a mixture (Fluid 15) tetrahydro Binor-S. The results of the measurements of the properties and the traction coefficient are shown in Table 1.

Example 32

Fluid 15 of Example 31 was blended with Fluid B of Comparative Example 2 so that the amount of the Fluid 15 was 50% by mass of the blend. The results of the measurements of the properties and the traction coefficient are shown in Table 1.

TABLE 1-3

|  | Example 7<br>Fluid 3 | Example 8<br>Fluid 3 + Fluid B | Example 9<br>Fluid 4 | Example 10<br>Fluid 4 + Fluid B | Example 11<br>Fluid 5 | Example 12<br>Fluid 5 + Fluid B |
|---|---|---|---|---|---|---|
| Kinematic viscosity @ 40° C. mm$^2$/s | 4.732 | 12.63 | 5.684 | 13.36 | 6.362 | 13.72 |
| Kinematic viscosity @ 100° C. mm$^2$/s | 1.724 | 3.016 | 1.911 | 3.106 | 2.086 | 3.169 |
| Viscosity index | — | 89 | — | 86 | 134 | 88 |
| Pour point ° C. | −50> | −50> | −50> | −50> | −50> | −50> |
| Low temperature viscosity @ −40° C. Pa•s | 1> | 4 | 1> | 5 | 1> | 6 |
| Density g/cm$^3$ | 0.9224 | 0.9478 | 0.9429 | 0.9521 | 0.9272 | 0.9488 |
| Traction coefficient @ 120° C. | 0.062 | 0.081 | 0.068 | 0.082 | 0.062 | 0.081 |
| Remarks |  | Fluid 3: 20% by mass |  | Fluid 4: 20% by mass |  | Fluid 5: 20% by mass |

TABLE 1-4

|  | Example 13<br>Fluid 6 | Example 14<br>Fluid 6 + Fluid B | Example 15<br>Fluid 7 | Example 16<br>Fluid 7 + Fluid B | Example 17<br>Fluid 8 | Example 18<br>Fluid 8 + Fluid B |
|---|---|---|---|---|---|---|
| Kinematic viscosity @ 40° C. mm$^2$/s | 13.48 | 15.25 | 5.563 | 13.26 | 7.024 | 14.07 |
| Kinematic viscosity @ 100° C. mm$^2$/s | 3.342 | 3.458 | 1.938 | 3.115 | 2.259 | 3.231 |
| Viscosity index | 121 | 102 | — | 91 | 143 | 91 |
| Pour point ° C. | −50> | −50> | −50> | −50> | −50> | −50> |
| Low temperature viscosity @ −40° C. P•as | 3 | 11 | 1> | 4 | 1> | 8 |
| Density g/cm3 | 0.9627 | 0.9585 | 0.9366 | 0.9508 | 0.9239 | 0.9481 |
| Traction coefficient @ 120° C. | 0.08 | 0.083 | 0.061 | 0.081 | 0.066 | 0.082 |
| Remarks |  | Fluid 6: 50% by mass |  | Fluid 7: 20% by mass |  | Fluid 8: 20% by mass |

TABLE 1-5

|  | Example 19<br>Fluid 9 | Example 20<br>Fluid 9 + Fluid B | Example 21<br>Fluid 10 | Example 22<br>Fluid 10 + Fluid B | Example 23<br>Fluid 11 | Example 24<br>Fluid 11 + Fluid B |
|---|---|---|---|---|---|---|
| Kinematic viscosity @ 40° C. mm$^2$/s | 6.25 | 13.69 | 10.80 | 14.91 | 8.028 | 13.57 |
| Kinematic viscosity @ 100° C. mm$^2$/s | 2.141 | 3.193 | 2.894 | 3.35 | 2.28 | 2.28 |
| Viscosity index | 166 | 94 | 119 | 92 | 91 | 81 |
| Pour point ° C. | −50> | −50> | −50> | −50> | −50> | −50> |
| Low temperature viscosity @−40° C. Pa•s | 1> | 4 | 1> | 14 | 1> | 9 |
| Density g/cm$^3$ | 0.9383 | 0.9511 | 0.9486 | 0.9527 | 0.9953 | 0.9663 |
| Traction coefficient @ 120° C. | 0.045 | 0.078 | 0.072 | 0.082 | 0.070 | 0.081 |
| Remarks |  | Fluid 9: 20% by mass |  | Fluid 10: 30% by mass |  | Fluid 11: 30% by mass |

TABLE 1-6

|  | Example 25<br>Fluid 12 | Example 26<br>Fluid 12 + Fluid B | Example 27<br>Fluid 13 | Example 28<br>Fluid 13 + Fluid B | Example 29<br>Fluid 14 | Example 30<br>Fluid 14 + Fluid B | Example 31<br>Fluid 15 | Example 32<br>Fluid 15 + Fluid B |
|---|---|---|---|---|---|---|---|---|
| Kinematic viscosity @ 40° C. mm$^2$/s | 9.462 | 12.66 | 9.976 | 14.74 | 10.00 | 14.70 | 13.66 | 15.44 |
| Kinematic viscosity @ 100° C. mm$^2$/s | 2.503 | 2.977 | 2.716 | 3.306 | 2.722 | 3.302 | 3.378 | 3.481 |
| Viscosity index | 84 | 80 | 112 | 88 | 113 | 88 | 122 | 101 |
| Pour point ° C. | −50> | −50> | −25 | −45 | −25 | −45 | −25 | −45 |
| Low temperature viscosity @ −40° C. Pa•s | 1> | 2 | — | 15 | — | 15 | — | 14 |
| Density g/cm$^3$ | 0.9726 | 0.9634 | 1.0806 | 0.9891 | 1.0439 | 0.9796 | 1.0545 | 1.02 |

| | Example 25 Fluid 12 | Example 26 Fluid 12 + Fluid B | Example 27 Fluid 13 | Example 28 Fluid 13 + Fluid B | Example 29 Fluid 14 | Example 30 Fluid 14 + Fluid B | Example 31 Fluid 15 | Example 32 Fluid 15 + Fluid B |
|---|---|---|---|---|---|---|---|---|
| Traction coefficient @ 120° C. | 0.072 | 0.079 | 0.061 | 0.079 | 0.070 | 0.081 | 0.080 | 0.083 |
| Remarks | | Fluid 12: 50% by mass | | Fluid 13: 30% by mass | | Fluid 14: 30% by mass | | Fluid 15: 50% by mass |

INDUSTRIAL APPLICABILITY

The lube base oil and lubricating oil composition of the present invention satisfy the coefficient of high-temperature traction, low-temperature fluidity and viscosity index at a high level and are suitably used as a traction drive fluid for CVT (continuously variable transmission) for automobiles.

The invention claimed is:

1. A composition comprising 1-60% by mass of at least one hydrocarbon compound of any of formulas (a) to (f),

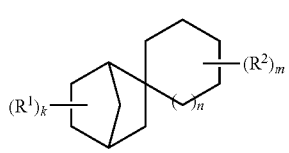
(a)

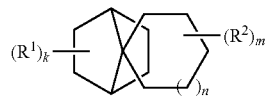
(b)

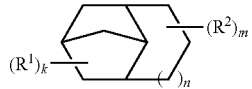
(c)

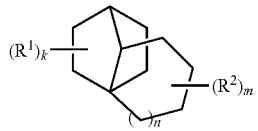
(d)

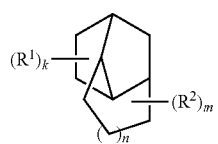
(e)

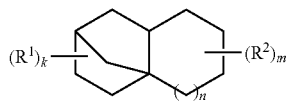
(f)

wherein in (a)-(f), k, m and n are each an integer of 0 to 6 with the proviso that k+m is an integer of 0 to 6, and wherein $R^1$ and $R^2$ each represent an alkyl group having 1 to 4 carbon atoms or a cycloalkyl group having 5 to 12 carbon atoms;

and a synthetic traction base oil which is selected from the group consisting of:

a hydrocarbon which has 16 to 20 carbon atoms and which is represented by the formula (h):

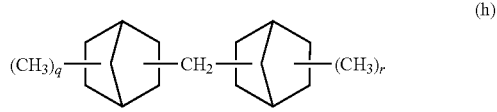
(h)

wherein q is an integer of 1 or 2 and r is an integer of 2 or 3, 2,4-dicyclohexyl-2-methylpentane, and 2,3-dicyclohexyl-2,3-dimethylbutane, wherein the composition has a viscosity, at −40° C., of 40 Pa·s or lower, and a viscosity index of 80 or higher.

2. The composition as recited in claim 1, wherein the synthetic traction base oil having an alicyclic structure is a hydrocarbon which has 16 to 20 carbon atoms and which is represented by the formula (h):

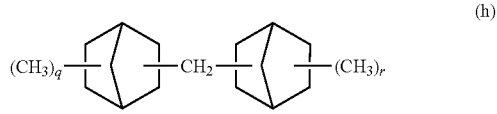
(h)

wherein q is an integer of 1 or 2 and r is an integer of 2 or 3.

3. The composition as recited in claim 1, wherein the synthetic traction base oil having an alicyclic structure is 2,4-dicyclohexyl-2-methylpentane.

4. The composition as recited in claim 1, wherein the synthetic traction base oil having an alicyclic structure is 2,3-dicyclohexyl-2,3-dimethylbutane.

5. The composition of claim 1, further comprising at least one additive selected from the group consisting of an antioxidant, a viscosity index improver, a detergent dispersant, a friction reducing agent, a metal deactivator, a pour point depressant, an abrasion proof agent, an antifoaming agent and an extreme pressure agent.

6. The composition as recited in claim 1, wherein the composition has a viscosity, at −40° C., of 30 Pa·s or lower.

7. The composition as recited in claim 1, comprising a hydrocarbon compound of formula (a).

8. The composition as recited in claim 1, comprising a hydrocarbon compound of formula (b).

9. The composition as recited in claim 1, comprising a hydrocarbon compound of formula (c).

10. The composition as recited in claim 1, comprising a hydrocarbon compound of formula (d).

11. The composition as recited in claim 1, comprising a hydrocarbon compound of formula (e).

12. The composition as recited in claim 1, comprising a hydrocarbon compound of formula (f).

13. The composition as recited in claim 2, comprising a hydrocarbon compound of formula (a).

14. The composition as recited in claim 2, comprising a hydrocarbon compound of formula (b).

15. The composition as recited in claim 2, comprising a hydrocarbon compound of formula (c).

16. The composition as recited in claim 2, comprising a hydrocarbon compound of formula (d).

17. The composition as recited in claim 2, comprising a hydrocarbon compound of formula (e).

18. The composition as recited in claim 2, comprising a hydrocarbon compound of formula (f).

* * * * *